United States Patent
Gou et al.

(10) Patent No.: US 12,138,484 B2
(45) Date of Patent: Nov. 12, 2024

(54) METHOD AND SYSTEM FOR CHECKING CONSISTENCY BETWEEN RADIOTHERAPY EQUIPMENT ISOCENTER AND TREATMENT ISOCENTER

(71) Applicants: OUR UNITED CORPORATION, Xi'an (CN); SHENZHEN OUR NEW MEDICAL TECHNOLOGIES DEVELOPMENT CO., LTD., Shenzhen (CN)

(72) Inventors: Tianchang Gou, Xi'an (CN); Jinsheng Li, Shenzhen (CN); Hao Yan, Xi'an (CN)

(73) Assignees: Our United Corporation, Shaanxi (CN); Shenzhen Our New Medical Technologies Development Co., Ltd., Shenzhen (CN)

( * ) Notice: Subject to any disclaimer, the term of this patent is extended or adjusted under 35 U.S.C. 154(b) by 977 days.

(21) Appl. No.: 17/259,913

(22) PCT Filed: Feb. 1, 2019

(86) PCT No.: PCT/CN2019/074509
§ 371 (c)(1),
(2) Date: Jan. 12, 2021

(87) PCT Pub. No.: WO2020/010842
PCT Pub. Date: Jan. 16, 2020

(65) Prior Publication Data
US 2021/0290981 A1    Sep. 23, 2021

(30) Foreign Application Priority Data
Jul. 12, 2018 (WO) ................ PCT/CN2018/095470

(51) Int. Cl.
*A61N 5/10* (2006.01)
*G06T 11/00* (2006.01)

(52) U.S. Cl.
CPC ......... *A61N 5/1075* (2013.01); *A61N 5/1042* (2013.01); *A61N 5/1045* (2013.01);
(Continued)

(58) Field of Classification Search
CPC ........ A61N 5/10; A61N 5/103; A61N 5/1031; A61N 5/1037; A61N 5/1042;
(Continued)

(56) References Cited

U.S. PATENT DOCUMENTS 5,651,043 A * 7/1997 Tsuyuki ............... A61N 5/1042
378/65
6,392,978 B1  5/2002 Sato
(Continued)

FOREIGN PATENT DOCUMENTS

CN   101209368 A   7/2008
CN   102052895 A   5/2011
(Continued)

OTHER PUBLICATIONS

International search report of PCT application No. PCT/CN2019/074509 issued on Apr. 28, 2019.
(Continued)

*Primary Examiner* — Allen C. Ho
(74) *Attorney, Agent, or Firm* — Knobbe, Martens, Olson & Bear, LLP (57) ABSTRACT

Provided is a method for checking consistency between a radiotherapy equipment isocenter and a treatment isocenter, wherein the method includes: acquiring projection data from a detector and generating image data based on the projection data, wherein the image data includes a light spot and a shading located in the light spot, and the light spot and the
(Continued)

--- acquiring, by a processing device, projection data from a detector and generating image data based on the projection data, wherein the image data includes a light spot and a shading located in the light spot, and the light spot and the shading are formed by a radiation beam generated by a treatment head of the radiotherapy equipment and then being blocked by a radiation blocking body — 201

↓ determining, by the processing device, an offset between the radiotherapy equipment isocenter and the treatment isocenter based on the image data — 202 shading are formed by a radiation beam generated by a treatment head of the radiotherapy equipment and then being blocked by a radiation blocking body; and determining an offset between the radiotherapy equipment isocenter and the treatment isocenter based on the image data. A system and a device for checking consistency between a radiotherapy equipment isocenter and a treatment isocenter are also provided.

20 Claims, 4 Drawing Sheets (52) U.S. Cl.
CPC ......... *A61N 5/1047* (2013.01); *A61N 5/1049* (2013.01); *A61N 5/1081* (2013.01); *G06T 11/006* (2013.01); *A61N 2005/1056* (2013.01); *A61N 2005/1076* (2013.01); *G06T 2211/436* (2013.01)

(58) Field of Classification Search
CPC .. A61N 5/1045; A61N 5/1047; A61N 5/1048; A61N 5/1049; A61N 2005/1054; A61N 5/1064; A61N 2005/1074; A61N 5/1075; A61N 2005/1076; A61N 5/1081; A61N 2005/1056
USPC .......................................................... 378/65
See application file for complete search history.

(56) References Cited

U.S. PATENT DOCUMENTS

| | | | | |
|---|---|---|---|---|
| 7,349,523 | B2* | 3/2008 | Jenkins | A61N 5/1048 378/65 |
| 7,356,120 | B2* | 4/2008 | Main | A61N 5/1048 378/65 |
| 8,395,980 | B2* | 3/2013 | Komma | G11B 7/1381 369/112.22 |
| 8,488,862 | B2* | 7/2013 | Bose | A61N 5/1075 378/163 |
| 9,616,251 | B2* | 4/2017 | Filiberti | A61N 5/107 |
| 9,636,079 | B2* | 5/2017 | Bredno | A61B 6/58 |
| 9,895,125 | B2* | 2/2018 | Besson | A61B 6/4435 |
| 10,039,519 | B2* | 8/2018 | Brown | A61B 6/584 |
| 10,569,105 | B2* | 2/2020 | Kilby | A61N 5/1075 |
| 10,932,748 | B2* | 3/2021 | Woods | A61B 6/08 |
| 11,173,324 | B2* | 11/2021 | Paysan | G06T 11/008 |
| 11,224,765 | B2* | 1/2022 | Mead | A61B 6/582 |
| 11,400,317 | B2* | 8/2022 | Yang | A61N 5/1081 |
| 11,607,564 | B2* | 3/2023 | Wösle | A61N 5/1049 |
| 12,005,273 | B2* | 6/2024 | Li | A61N 5/1075 |
| 2006/0002519 | A1 | 1/2006 | Jenkins et al. | |
| 2007/0071176 | A1 | 3/2007 | Main et al. | |
| 2012/0151508 | A1 | 6/2012 | Komma et al. | |
| 2015/0103972 | A1 | 4/2015 | Bredno et al. | |
| 2016/0023019 | A1 | 1/2016 | Filiberti et al. | |
| 2016/0114190 | A1 | 4/2016 | Brown et al. | |
| 2016/0166223 | A1 | 6/2016 | Besson | |
| 2019/0054322 | A1 | 2/2019 | Yang | |

FOREIGN PATENT DOCUMENTS

| | | |
|---|---|---|
| CN | 102103757 A | 6/2011 |
| CN | 103768724 A | 5/2014 |
| CN | 103776375 A | 5/2014 |
| CN | 104415459 A | 3/2015 |
| CN | 105473181 A | 4/2016 |
| CN | 105944242 A | 9/2016 |
| CN | 106215331 A | 12/2016 |
| CN | 107358607 A | 11/2017 |
| CN | 107510898 A | 12/2017 |
| CN | 107596578 A | 1/2018 |
| CN | 107684669 A | 2/2018 |
| CN | 107693958 A | 2/2018 |
| CN | 107875524 A | 4/2018 |
| GB | 201318974 | 12/2013 |
| JP | H0679006 A | 3/1994 |
| JP | H08112367 A | 5/1996 |
| JP | 2001074632 A | 3/2001 |
| JP | 2013046709 A | 3/2013 |
| WO | 2004034909 A1 | 4/2004 |

OTHER PUBLICATIONS

China National Intellectual Property Administration, First office action of Chinese application No. 201980046556.5 Issued on May 25, 2022, which is foreign counterpart application of this US application.
International search report of PCT application No. PCT/CN2018/095470 issued on Mar. 6, 2019.
China National Intellectual Property Administration, Notification to grant patent right for invention of Chinese application No. 201980046556.5 issued on Jan. 4, 2023, which is foreign counterpart application of this US application.
Shaojie Tang et al., Analytic Calculation of CT Phantom Projections and Its Application in Beam Hardening Correction, Journal of Xi'an Jiaotong University, vol. 42 No. 6, Jun. 30, 2008, entire document.

* cited by examiner

FIG. 1

| | |
|---|---|
| acquiring, by a processing device, projection data from a detector and generating image data based on the projection data, wherein the image data includes a light spot and a shading located in the light spot, and the light spot and the shading are formed by a radiation beam generated by a treatment head of the radiotherapy equipment and then being blocked by a radiation blocking body | 201 |
| determining, by the processing device, an offset between the radiotherapy equipment isocenter and the treatment isocenter based on the image data | 202 |

METHOD AND SYSTEM FOR CHECKING CONSISTENCY BETWEEN RADIOTHERAPY EQUIPMENT ISOCENTER AND TREATMENT ISOCENTER

The present disclosure is a US national phase application of PCT Application No. PCT/CN2019/074509, filed on Feb. 1, 2019, which claims priority to PCT Application No. PCT/CN2018/095470, filed on Jul. 12, 2018 and entitled "METHOD AND SYSTEM FOR CHECKING CONSISTENCY BETWEEN RADIOTHERAPY EQUIPMENT ISOCENTER AND TREATMENT ISOCENTER", the contents of each of which are incorporated herein by reference in its entirety.

TECHNICAL FIELD

The present disclosure relates to the field of radiotherapy technologies, and more particularly relates to a method and system for checking consistency between radiotherapy equipment isocenter and a treatment isocenter.

BACKGROUND

The role and status of radiotherapy in tumor treatment have become increasingly prominent, and radiotherapy has become one of the main methods for the treatment of malignant tumors.

In order to ensure the precision of radiotherapy, it is necessary to regularly carry out isocenter verification for radiotherapy equipment, that is, check the consistency between radiotherapy equipment isocenter and a treatment isocenter. In traditional technologies, the film-based method is used for the isocenter verification.

SUMMARY

According to embodiments of the present disclosure, a method and system for checking consistency between a radiotherapy equipment isocenter and a treatment isocenter are provided. The technical solutions are as follows:

According to embodiments of the present disclosure, a method for checking consistency between a radiotherapy equipment isocenter and a treatment isocenter is provided. The method includes:

acquiring projection data from a detector and generating image data based on the projection data, wherein the image data includes a light spot and a shading located in the light spot, and the light spot and the shading are formed by a radiation beam generated by a treatment head of the radiotherapy equipment and then being blocked by a radiation blocking body; and determining an offset between the radiotherapy equipment isocenter and the treatment isocenter based on the image data.

Optionally, determining the offset between the radiotherapy equipment isocenter and the treatment isocenter based on the image data includes:

determining the offset between the radiotherapy equipment isocenter and the treatment isocenter based on an offset between the light spot and the shading in the image data.

Optionally, acquiring projection data from the detector and generating the image data based on the projection data includes:

acquiring, when a gantry of the radiotherapy equipment is rotated by a first preset angle, projection data corresponding to the first preset angle from the detector and generating first image data; and acquiring, when the gantry of the radiotherapy equipment is rotated by a second preset angle, projection data corresponding to the second preset angle from the detector and generating second image data, and wherein determining the offset between the radiotherapy equipment isocenter and the treatment isocenter based on the offset between the light spot and the shading in the image data includes:

determining a three-dimensional offset between the light spot and the shading based on a two-dimensional offset between the light spot and the shading in the first image data and a two-dimensional offset between the light spot and the shading in the second image data; and determining the offset between the radiotherapy equipment isocenter and the treatment isocenter based on the three-dimensional offset between the light spot and the shading.

Optionally, the image data includes a plurality of light spots and shadings located in each light spot, and wherein determining the offset between the radiotherapy equipment isocenter and the treatment isocenter based on the three-dimensional offset between the light spot and the shading includes:

determining an average offset based on three-dimensional offset between each light spot and the shading included therein in the image data; and determining the offset between the radiotherapy equipment isocenter and the treatment isocenter based on the average offset.

Optionally, the first preset angle differs from the second preset angle by 90 degrees.

Optionally, determining the offset between the radiotherapy equipment isocenter and the treatment isocenter based on the image data includes:

determining the offset between the radiotherapy equipment isocenter and the treatment isocenter based on an offset between a center point of the light spot and a center point of the shading in the image data.

Optionally, acquiring the projection data from the detector and generating the image data based on the projection data includes:

acquiring, each time a gantry of the radiotherapy equipment is rotated by a different angle relative to an initial position, projection data corresponding to each of the respective angles from the detector and generating image data corresponding to each of the respective angles, and wherein determining the offset between the radiotherapy equipment isocenter and the treatment isocenter based on the image data includes:

determining the offset between the radiotherapy equipment isocenter and the treatment isocenter based on the image data corresponding to each of the respective angles.

Optionally, determining the offset between the radiotherapy equipment isocenter and the treatment isocenter based on the image data corresponding to each of the respective angles includes:

determining the offset between the radiotherapy equipment isocenter and the treatment isocenter by back-projecting the image data corresponding to each of the respective angles to the radiotherapy equipment isocenter.

Optionally, determining the offset between the radiotherapy equipment isocenter and the treatment isocenter by back-projecting the image data corresponding to each of the respective angles to the radiotherapy equipment isocenter includes:

back-projecting the light spot in the image data corresponding to each of the respective angles to the radiotherapy equipment isocenter, and constructing a light spot body according to a three-dimensional reconstruction algorithm; and determining the offset between the radiotherapy equipment isocenter and the treatment isocenter based on an offset between a center of the light spot body and the therapy equipment isocenter.

Optionally, determining the offset between the radiotherapy equipment isocenter and the treatment isocenter by back-projecting the image data corresponding to each of the respective angles to the radiotherapy equipment isocenter includes:

back-projecting the light spot and the shading in the image data corresponding to each of the respective angles to the radiotherapy equipment isocenter, and constructing a light spot body and a shading body according to a three-dimensional reconstruction algorithm; and determining the offset between the radiotherapy equipment isocenter and the treatment isocenter based on an offset between a center of the light spot body and a center of the shading body.

Optionally, the gantry of the radiotherapy equipment is rotated by an angle of 0.5 degree every time.

Optionally, the shading formed from the radiation blocking body is a centrosymmetric pattern.

Optionally, the shading is in a circular shape, the light spot is in a circular shape, and a diameter of the light spot is greater than or equal to twice of a diameter of the shading.

According to embodiments of the present disclosure, a system for checking consistency between a radiotherapy equipment isocenter and a treatment isocenter is provided, wherein the system includes radiotherapy equipment, a radiation blocking body and a processing device, wherein:

the radiotherapy equipment includes a gantry, the gantry is provided with a treatment head and a detector mounted on a position opposite to the treatment head, and the detector is configured to receive a radiation beam generated by the treatment head and convert the radiation beam into projection data;

the radiation blocking body is detachably mounted at the radiotherapy equipment isocenter, and a center of the radiation blocking body coincides with the radiotherapy equipment isocenter; and the processing device is electrically connected to the detector, and the processing device is configured to execute the above methods for checking consistency between a radiotherapy equipment isocenter and a treatment isocenter.

Optionally, the radiation blocking body is a radiation blocking ball.

Optionally, the radiation blocking ball is a metal ball.

Optionally, the system further includes a checking phantom, the radiation blocking body is mounted at a central position of the checking phantom, and the radiation blocking body is detachably mounted at the radiotherapy equipment isocenter by means of the checking phantom.

Optionally, the radiotherapy equipment further includes a treatment couch, and the checking phantom is detachably mounted at a preset position on the treatment couch and is located at the radiotherapy equipment isocenter.

According to embodiments of the present disclosure, a device for checking consistency between a radiotherapy equipment isocenter and a treatment isocenter is provided, wherein the device includes a processor and a memory storing at least one instruction thereon, wherein the instruction is loaded and executed by the processor to implement the above methods for checking consistency between a radiotherapy equipment isocenter and a treatment isocenter.

According to embodiments of the present disclosure, a computer readable storage medium storing at least one instruction therein is provided, wherein the instruction is loaded and executed by a processor to implement the above methods for checking consistency between a radiotherapy equipment isocenter and a treatment isocenter.

BRIEF DESCRIPTION OF THE DRAWINGS

In order to describe the technical solutions of the embodiments of the present disclosure more clearly, the following briefly describes the accompanying drawings required for describing the embodiments. Apparently, the accompanying drawings as described below show merely some embodiments of the present disclosure, and a person of ordinary skill in the art may also derive other drawings from these accompanying drawings without creative efforts.

| Legend | |
| --- | --- |
| 1. | radiotherapy equipment |
| 2. | detector |
| 3. | radiation blocking body |
| 4. | processing device |
| 5. | checking phantom |
| 11. | gantry |
| 12. | treatment head |
| 13. | treatment couch |

DETAILED DESCRIPTION

In order to enable those skilled in the art to better understand the solutions of the embodiments of the present disclosure, the embodiments of the present disclosure are further described in detail below with reference to the accompanying drawings and embodiments.

Taking a stereotactic radiotherapy equipment as an example, the corresponding isocenter verification includes the followings.

Operator first places a checking phantom having a film installed therein at a preset position on the radiotherapy equipment, such that a pre-marked reference point on the film coincides with the isocenter of the radiotherapy equipment. Then, the stereotactic radiotherapy equipment irradiates the checking phantom, and a light spot formed by the convergence of a plurality of radiation beams is produced on the film, where the center of the light spot is the treatment isocenter. Subsequently, the film that have been irradiated by the radiation beams is taken out and scanned to determine an offset between the radiotherapy equipment isocenter and the treatment isocenter.

In the process of implementing the present disclosure, there are at least the following problems.

Every time the checking is carried out, a new film needs to be installed in the checking phantom. After being irradiated by the radiation beams, the film needs to be taken out and scanned to obtain digital image data. Finally, the operator analyzes the image data to obtain the offset between the radiotherapy equipment isocenter and the treatment isocenter.

As a result, the process of isocenter verification by the film-based method is rather cumbersome, and the checking efficiency is low.

The present disclosure provides a method and system for checking consistency between a radiotherapy equipment isocenter and a treatment isocenter. The method is applicable to check the precision of radiotherapy equipment. The precision of the radiotherapy equipment is represented by the degree of coincidence between a radiation beam generated by the radiotherapy equipment and a patient's tumor area, i.e., the higher the degree of coincidence is, the higher the precision of the radiotherapy equipment is. In practice, a patient lies down on a treatment couch, and the patient's tumor area corresponds to the radiotherapy equipment isocenter, i.e., the patient's tumor area is located at the radiotherapy equipment isocenter, and the converging point of radiation beams is called the treatment isocenter. If the treatment isocenter coincides with the radiotherapy equipment isocenter in a high degree, the radiation beams can accurately converge on the patient's tumor area. In embodiments, an isocenter verification method is configured to check the precision of the radiotherapy equipment, i.e., to verify the degree of coincidence between the treatment isocenter and the radiotherapy equipment isocenter.

The radiotherapy equipment isocenter is inherent to the radiotherapy equipment. Theoretically, the treatment isocenter should coincide with the radiotherapy equipment isocenter. However, once the radiotherapy equipment wears out or is otherwise damaged due to long-time use, the treatment isocenter may be not coincide with the radiotherapy equipment isocenter, thereby affecting the precision of the radiotherapy equipment.

Figure 1:
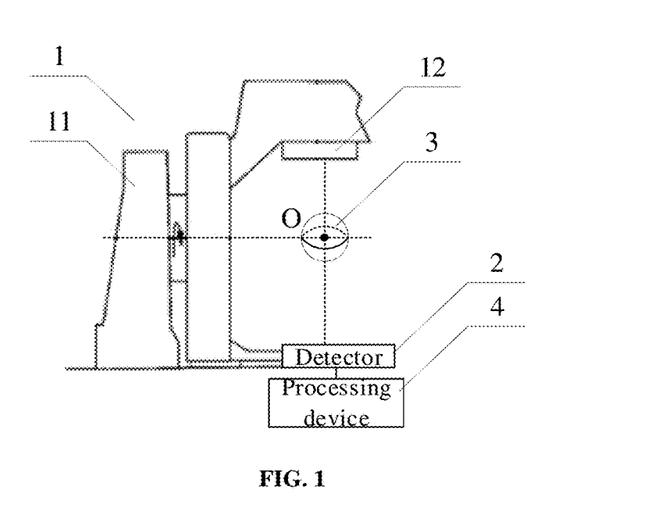
FIG. 1 is a schematic structural diagram of a system for checking consistency between a radiotherapy equipment isocenter and a treatment isocenter according to the embodiments of the present disclosure.

The method is applied to a system for checking consistency between a radiotherapy equipment isocenter and a treatment isocenter. The method is executed by a processing device in the system. As shown in FIG. 1, the system mainly includes radiotherapy equipment 1, a detector 2, a radiation blocking body 3 and a processing device 4. The radiotherapy equipment 1 includes a gantry 11 and a treatment head 12. The treatment head 12 and the detector 2 are both mounted on the gantry 11 of the radiotherapy equipment 1. The treatment head 12 is opposite to the position of the detector 2. For example, the position of the treatment head 12 and the position of the detector 2 are centrosymmetric with respect to the radiotherapy equipment isocenter. The radiation blocking body 3 is detachably mounted at a preset position on the radiotherapy equipment 1, and the center of the radiation blocking body 3 coincides with the radiotherapy equipment isocenter. The processing device 4 is electrically connected to the detector 2. The detector 2 is a device capable of acquiring projection data formed by a radiation beam generated by the radiotherapy equipment 1, for example, may be an electronic portal imaging device (EPID).

The radiation blocking body 3 is a structure that can block the penetration of rays, and is in the shape of a centrosymmetric pattern after projection. In this way, after the radiation blocking body 3 is projected at different angles, the position of the center point of the formed projection image can remain unchanged in the projection image. For example, the radiation blocking body 3 is projected at a certain initial position, and the center of the formed projection image is at the central position of the projection image; then, after being rotated by a certain angle (e.g., 10 degrees or 15 degrees) relative to the initial position, the radiation blocking body 3 is projected again, and the position of the center point of the obtained projection image in the projection image is still at the central position. For example, the radiation blocking body 3 is of a spherical structure, the obtained projection image is in the shape of a circle and the center point of the circle is at the central position of the projection image when the radiation blocking body 3 of the spherical structure is projected at any angle. The specific shape of the radiation blocking body 3 is not limited in this embodiment. The radiation blocking body 3 of the spherical structure is taken as an example for the ease of description, other situations are similar and the details are not repeated herein.

Figure 2:
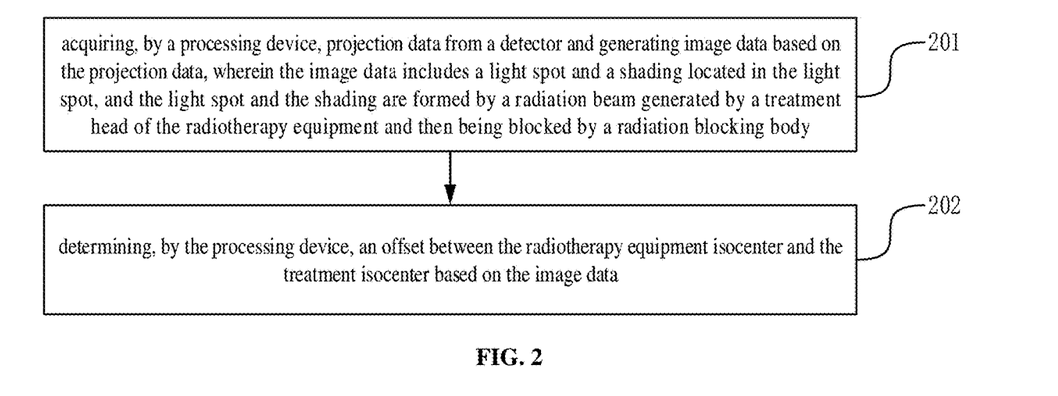
FIG. 2 is a schematic flowchart of a method for checking consistency between a radiotherapy equipment isocenter and a treatment isocenter according to the embodiments of the present disclosure.

As shown in FIG. 2, the method is executed as follows.

In step 201, the processing device 4 acquires projection data from the detector 2 and generates image data based on the projection data, wherein the image data includes a light spot and a shading located in the light spot, and the light spot and the shading are formed by a radiation beam generated by the treatment head 12 of the radiotherapy equipment 1 and then being blocked by a radiation blocking body 3.

In order to meet the requirements of the image data, the shading is located in the light spot, and the size of the light spot is much larger than the size of the shading. For example, in the case that the radiation blocking body 3 is a radiation blocking ball, the shape of the shading formed by the radiation blocking body 3 is circular. If the shape of the light spot is also circular, the diameter of the light spot is greater than that of the shading. In order to improve the accuracy of checking, correspondingly, the diameter of the light spot is much greater than the diameter of the shading, for example, the diameter of the light spot is greater than or equal to twice of the diameter of the shading.

Figure 3:
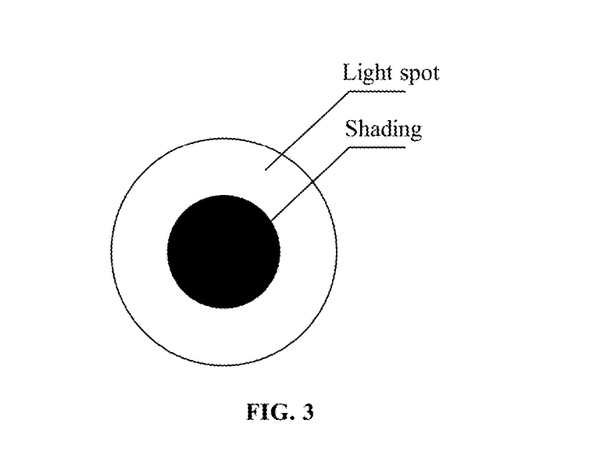
FIG. 3 is a schematic structural diagram of a light spot and a shading according to an embodiment of the present disclosure.

In one embodiment, the diameter of the light spot formed by the radiation beam generated by the treatment head 12 of the radiotherapy equipment 1 is greater than the diameter of the radiation blocking body 3. As shown in FIG. 1, the irradiation of the radiation beam on the detector 2 is partly blocked by the radiation blocking body 3, such that the detector 2 can acquire projection data formed by the radiation beam, and send the projection data to the processing device 4. After receiving the projection data, the processing device 4 converts the projection data into image data. Since the radiation blocking body 3 can block the penetration of the radiation beam, as shown in FIG. 3, the light spot in the image data has a shading therein.

In step 202, the processing device 4 determines an offset between the radiotherapy equipment isocenter and the treatment isocenter based on the image data.

In one embodiment, the light spot is generated by the radiation beam, and the radiation beam is used to kill tumor cells, such that the center point of the light spot can represent the treatment isocenter. The sphere center of the radiation blocking body 3 coincides with the radiotherapy equipment isocenter, such that the center point of the shading can represent the radiotherapy equipment isocenter. Therefore, one method for determining the offset between the radiotherapy equipment isocenter and the treatment isocenter may be that the processing device 4 determines the offset between the radiotherapy equipment isocenter and the treatment isocenter based on an offset between the light spot and the shading in the image data. The following will also describe other methods for determining the offset between the radiotherapy equipment isocenter and the treatment isocenter.

In summary, when consistency between a radiotherapy equipment isocenter and a treatment isocenter is checked by the above method, the processing device, after acquiring projection data including a light spot representative of the treatment isocenter and a shading representative of the radiotherapy equipment isocenter, directly converts the projection data into image data without the participation of operator; then the processing device determines an offset between the treatment isocenter and the radiotherapy equipment isocenter based on an offset between the light spot and the shading. As can be seen, in comparison with the checking of consistency between a radiotherapy equipment isocenter and a treatment isocenter by using a film in the related art, the radiation blocking body is not affected by the radiation beam and does not need to be frequently replaced, and the processing device directly converts the projection data into image data without the participation of operator. Therefore, the method simplifies the checking process, and further improves the checking efficiency.

Optionally, the processing device 4 can determine the offset between the radiotherapy equipment isocenter and the treatment isocenter based on the offset between the light spot and the shading by various methods. For example, one method is that the offset between the radiotherapy equipment isocenter and the treatment isocenter is determined based on an offset between a center point of the light spot and a center point of the shading in the image data. This method is relatively simple, because the center point of the light spot coincides with the treatment isocenter, the center point of the radiation blocking body 3, i.e., the center point of the shading coincides with the radiotherapy equipment isocenter, and in general, the position of the center point of the center point can be easily determined with high accuracy. Therefore, the offset between the radiotherapy equipment isocenter and the treatment isocenter can be determined according to the offset between the center of the light spot and the center of the shading.

For another example, the offset between the radiotherapy equipment isocenter and the treatment isocenter may be determined according to an offset between edges of the light spot and the shading at corresponding positions. Specifically, the processing device 4 can first determine an edge of the light spot according to a contour of the light spot and determine an edge of the shading according to a contour of the shading, and then determine the offset between the radiotherapy equipment isocenter and the treatment isocenter according to an offset between the edges of the light spot and the shading at corresponding positions.

Optionally, the radiotherapy equipment 1 generally includes a single-source radiotherapy equipment and a multi-source radiotherapy equipment. For the single-source radiotherapy equipment, the treatment head 12 is provided with only one radiation source, and correspondingly one radiation beam is generated, and one light spot is formed. For the multi-source radiotherapy equipment, the treatment head 12 is provided with a plurality of radiation sources, which can generate multiple radiation beams, and the corresponding image data can include a plurality of light spots having a shading therein. In this case, the processing device 4 first determines an average offset based on an offset between each light spot and the shading included therein in the image data, and then determine the offset between the radiotherapy equipment isocenter and the treatment isocenter based on the average offset.

Figure 8:
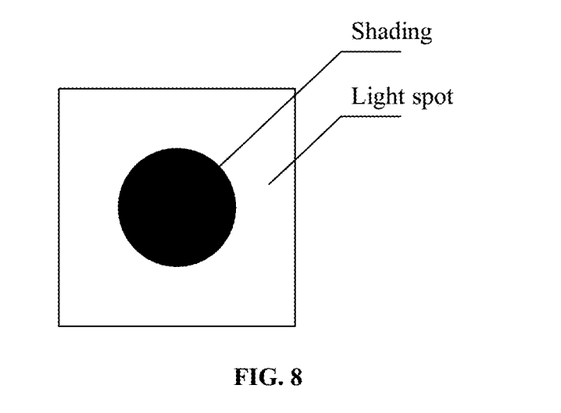
FIG. 8 is a schematic structural diagram of a light spot and a shading according to another embodiment of the present disclosure.

For example, when the treatment head 12 is provided with 13 radiation sources, 13 radiation beams are generated, and the converging point of the 13 radiation beams is the treatment isocenter. In this case, energy accumulated by the radiation beams at the treatment isocenter is also very high compared to that of one radiation source. All the 13 radiation beams pass by the radiation blocking body 3 disposed on the radiotherapy equipment isocenter. Correspondingly, as shown in FIG. 8, the projection data generated by the detector 2 includes 13 light spots having a shading therein, and therefore the image data generated by the processing device 4 includes 13 light spots having a shading therein. Subsequently, the processing device 4 can determine an average offset based on an offset between each light spot and the shading included therein in the image data, where the average offset may be an arithmetic average offset or a weighted average offset. Moreover, since the processing device 4 can determine the offset between the light spot and the shading that correspond to each radiation source, it can determine an offset between a treatment isocenter generated by each radiation source and the radiotherapy equipment isocenter, and further can fine-tune each radiation source based on the offset, so as to increase the degree of coincidence between the treatment isocenter of each radiation source and the radiotherapy equipment isocenter.

As can be seen, for the multi-source radiotherapy equipment, in the process of determining the offset between the radiotherapy equipment isocenter and the treatment isocenter by the method, the offset between the light spot and the shading that correspond to each radiation source can also be obtained. Therefore, operator can adjust the radiation sources in a targeted fashion, for example, adjust a collimator the offset of which is not within a preset value range. In the method of checking the precision of the radiotherapy equipment by a film in the prior art, radiation beams generated by a plurality of radiation sources first converge and then irradiate the film. It can be seen that the offset of a single radiation source cannot be distinguished by the film. Therefore, for the multi-source radiotherapy equipment, in comparison with the checking method using a film in the prior art, the present method can detect the offset of a single radiation source, enabling operator to adjust the radiotherapy equipment in a targeted fashion and reduce the checking time for the operator, thereby improving the efficiency of checking the consistency between the radiotherapy equipment isocenter and the treatment isocenter.

Optionally, since both the radiotherapy equipment isocenter and the treatment isocenter are points in a three-dimensional space, offsets between the two in the three-dimensional space, i.e., offsets on x axis, y axis and z axis, need to be determined, so as to determine the offset between the two. Since the projection data acquired by the detector 2 is two-dimensional, correspondingly, the detector 2 can acquire projection data once from each of two two-dimensional coordinate systems, determine offsets in the two two-dimensional coordinate systems, and then further determine the offset in the three-dimensional coordinate system including the two two-dimensional coordinate systems. For example, x-axis and y-axis offsets in a two-dimensional coordinate system xoy are determined first, and then y-axis and z-axis offsets in a two-dimensional coordinate system yoz are determined; thus, x-axis, y-axis and z-axis offsets in the three-dimensional coordinate system are determined. Correspondingly, the processing device 4 can be executed according to the process shown in FIG. 4.

Figure 4:
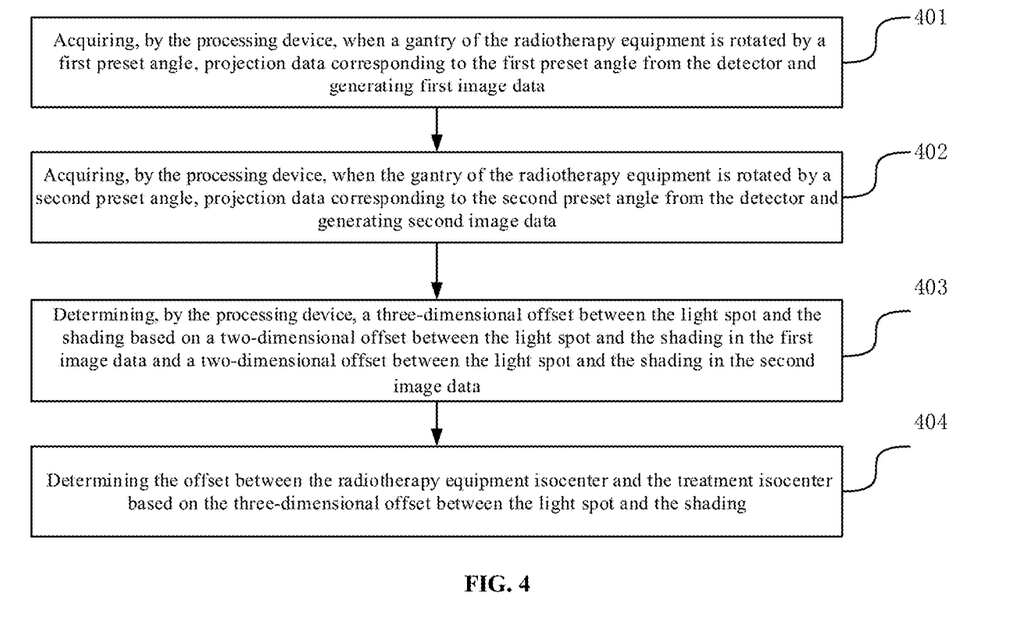
FIG. 4 is a schematic flowchart of a method for checking consistency between a radiotherapy equipment isocenter and a treatment isocenter according to another embodiment of the present disclosure.

In step 401, when the gantry 11 of the radiotherapy equipment 1 is rotated by a first preset angle, the processing device 4 acquires projection data corresponding to the first preset angle from the detector 2 and generates first image data.

The position of the gantry 11 of the radiotherapy equipment 1 after being rotated by the first preset angle is called an initial position. At the initial position, the angle of the rotation of the gantry 11 can be recorded as 0 degrees. Subsequently, the gantry 11 is rotated based on the initial position, i.e., the initial position is the position where the gantry 11 starts to rotate.

In one embodiment, generally, in order to reduce the number of treatment heads 12 to reduce costs, the gantry 11 is designed into a rotatable gantry 11, as shown in FIG. 1. The horizontal dashed line in FIG. 1 represents the axis of rotation of the gantry 11. In this way, the gantry 11 is rotatable during radiotherapy by the radiotherapy equipment 1, so that the radiation beam generated by the radiotherapy equipment 1 is directed to the patient's target cell position (e.g., tumor position) at different angles. The first preset angle may be any angle. The first preset angle is the angle when the gantry 11 is at the initial position. When the gantry 11 is rotated by the first preset angle, i.e., when the gantry 11 is at the initial position, the first image data acquired by the processing device 4 is recorded as image data in the xoy plane.

In step 402, when the gantry 11 of the radiotherapy equipment 1 is rotated by a second preset angle, the processing device 4 acquires projection data corresponding to the second preset angle from the detector 2 and generates second image data.

The angle difference between the first preset angle and the second preset angle can be set arbitrarily, for example, may be ±90 degrees or ±120 degrees. The symbol "±" indicates the direction of rotation of the second preset angle relative to the first preset angle. The angle difference between the first preset angle and the second preset angle is not limited in this embodiment. 90 degrees is taken as an example for the ease of illustration, and other situations are similar, so the details are not repeated here.

In one embodiment, the second preset angle may be a certain angle rotated based on the first preset angle, for example, may be an angle which is rotated 90 degrees counterclockwise or clockwise based on the first preset angle, and correspondingly the difference between the first preset angle and the second preset angle is 90 degrees. As the first image data is recorded as the image data in the xoy plane, the second image data may be image data in the yoz plane or in the xoz plane.

In step 403, the processing device 4 determines a three-dimensional offset between the light spot and the shading based on a two-dimensional offset between the light spot and the shading in the first image data and a two-dimensional offset between the light spot and the shading in the second image data.

The two-dimensional offset is an offset in a two-dimensional plane, for example, may include an x-axis offset and a y-axis offset. The three-dimensional offset is an offset in a three-dimensional plane, for example, may include x-axis, y-axis and z-axis offsets.

In one embodiment, the processing device 4 determines position coordinates of the center points of the light spot and the shading in the two-dimensional plane corresponding to the first preset angle by using a two-dimensional normal distribution, and then determine the two-dimensional offset between the light spot and the shading at the first preset angle. Similarly, the processing device 4 also determines position coordinates of the center points of the light spot and the shading in the two-dimensional plane corresponding to the second preset angle by using the two-dimensional normal distribution, and then determine the two-dimensional offset between the light spot and the shading at the second preset angle. The processing device 4, after determining the two-dimensional offset between the light spot and the shading in the first image data and the two-dimensional offset between the light spot and the shading in the second image data, further determines an offset between the light spot and the shading in a three-dimensional space, i.e., the three-dimensional offset.

In step 404, the offset between the radiotherapy equipment isocenter and the treatment isocenter is determined based on the three-dimensional offset between the light spot and the shading.

In one embodiment, as described above, the offset between the light spot and the shading represents the offset between the radiotherapy equipment isocenter and the treatment isocenter. Therefore, the processing device 4, after determining the three-dimensional offset between the light spot and the shading, also determines the offset between the radiotherapy equipment isocenter and the treatment isocenter in the three-dimensional space.

Based on the above, for the treatment head 12 including 13 radiation sources, when the gantry 11 is at the initial position, the processing device 4 acquires image data including 13 light spots and shadings. After the gantry 11 is rotated by 90 degrees relative to the initial position, the processing device 4 acquires another image data including 13 light spots and shadings. In this case, the processing device 4 obtains the three-dimensional offset between each light spot and the corresponding shading based on the image data at the two angles. Then the processing device 4 determines the offset between the treatment isocenter and the radiotherapy equipment isocenter based on 13 sets of three-dimensional offsets. For example, an average offset (which may be a weighted average offset) may be determined based on the three-dimensional offset between each light spot and the corresponding shading in the image data; then the processing device 4 determines the offset between the treatment isocenter and the radiotherapy equipment isocenter based on the average offset.

In addition, the processing device 4 not only can determine the offset between the treatment isocenter generated by the treatment head 12 and the radiotherapy equipment isocenter, but also can determine the offset between the treatment isocenter generated by each radiation source in the treatment head 12 and the radiotherapy equipment isocenter. In this way, a technician can coarsely adjust the treatment head 12 based on the offset between the treatment isocenter generated by the treatment head 12 and the radiotherapy equipment isocenter, and then fine-tune each radiation source in the treatment head 12 based on the offset between the treatment isocenter generated by each radiation source in the treatment head 12 and the radiotherapy equipment isocenter. Thus, the accuracy of checking the radiotherapy equipment can be improved.

Optionally, in addition to the above method, the processing device 4 can also determine the offset between the treatment isocenter and the radiotherapy equipment isocenter by back-projection. The back-projection method may be as follows: first, each time when the gantry 11 of the radiotherapy equipment is rotated by a different angle relative to an initial position, the processing device 4 acquires projection data corresponding to each angle from the detector 2 and generating image data corresponding to each angle; then the processing device 4 determines an offset between the radiotherapy equipment isocenter and the treatment isocenter based on the image data corresponding to each of the respective angles.

In one embodiment, the processing device 4 determines one batch of corresponding image data at each position of the gantry 11. For example, before the gantry 11 starts to rotate, the processing device 4 determines one batch of corresponding image data, and then, each time the gantry 11 rotates, the processing device 4 determines another batch of corresponding image data. As such, if the gantry 11 rotates n times, the processing device 4 can acquire (n+1) batches of image data, which are all two-dimensional image data (i.e., planar image data). The processing device 4 may determine the offset between the radiotherapy equipment isocenter and the treatment isocenter based on the determined multiple batches of image data. For example, the offset may be determined by the above method, or may be determined by using a back-projection reconstruction algorithm, which includes: back-projecting the image data corresponding to each of the respective angles to the radiotherapy equipment isocenter, and determining the offset between the radiotherapy equipment isocenter and the treatment isocenter.

Back-projecting to the radiotherapy equipment isocenter means back-projecting the image data corresponding to each angle to a three-dimensional coordinate system established with the radiotherapy equipment isocenter as the origin of coordinates. The image data corresponding to each angle is image data in a two-dimensional space. In other words, the image data corresponding to each angle is planar image data.

In one embodiment, the processing device 4, after back-projecting the image data to the radiotherapy equipment isocenter, determines the three-dimensional image data in the above-mentioned three-dimensional coordinate system by a three-dimensional reconstruction algorithm, and then, determines the offset between the radiotherapy equipment isocenter and the treatment isocenter based on the three-dimensional image data after reconstruction.

The three-dimensional reconstruction algorithm is also called a back-projection reconstruction algorithm, i.e., an algorithm that uses information in a plurality of two-dimensional images to reconstruct three-dimensional information, such as a filtered back projection (FBP) three-dimensional reconstruction algorithm, a Feldkamp-Davis-Kress (FDK) three-dimensional reconstruction algorithm, again, and a Tent-FDK (T-FDK) three-dimensional reconstruction algorithm.

Optionally, since the radiation blocking body 3 is placed at the radiotherapy equipment isocenter, the processing device 4 can acquire parameter information of the radiotherapy equipment isocenter, and accordingly, the shading in the image data does not need to be reconstructed but only the light spot needs to be reconstructed. Correspondingly, the processing device 4 may back-project a light spot in the image data corresponding to each of the respective angles to the radiotherapy equipment isocenter, and construct a light spot body according to a three-dimensional reconstruction algorithm; then the processing device determines the offset between the radiotherapy equipment isocenter and the treatment isocenter according to an offset between a center of the light spot body and the radiotherapy equipment isocenter.

The light spot body is a virtual three-dimensional body constructed by using a three-dimensional reconstruction algorithm after back-projecting the light spot in the image data at each angle to the radiotherapy equipment isocenter. The shape of the light spot body is related to the shape of the light spot. For example, if a radiation beam emitted by a radiation source in the treatment head 12 is cylindrical and the light spot in the image data is circular, the more times the gantry 11 rotates, the closer the constructed light spot body is to a spherical shape.

In one embodiment, the processing device 4, after constructing the light spot body in the three-dimensional coordinate system with the radiotherapy equipment isocenter as the origin of coordinates, determines position coordinates information of the center point of the light spot body, further determines the three-dimensional offset between the light spot body and the radiotherapy equipment isocenter. Since the center point of the light spot body can represent the treatment isocenter, the processing device 4 can determine the offset between the radiotherapy equipment isocenter and the treatment isocenter.

Optionally, the processing device 4 can also back-project both the light spot and the shading, which may include: first, the processing device 4 back-projects a light spot and a shading in the image data corresponding to each of the respective angles to the radiotherapy equipment isocenter, and constructs a light spot body and a shading body according to a three-dimensional reconstruction algorithm; then the processing device 4 determines the offset between the radiotherapy equipment isocenter and the treatment isocenter according to an offset between a center of the light spot body and a center of the shading body.

The shading body is a virtual three-dimensional body constructed by using a three-dimensional reconstruction algorithm after back-projecting the shading in the image data at each angle to the radiotherapy equipment isocenter. The shape of the shading body is related to the shape of the radiation blocking body 3. For example, in the case that the gantry 11 rotates a large number of times, the shape of the shading body constructed is close to a sphere if the radiation blocking body 3 is a radiation blocking ball; the shape of the shading body constructed is close to a cube if the radiation blocking body 3 is a cube. In other words, the more times the gantry 11 rotates, the closer the shape of the shading body constructed is to the shape of the radiation blocking body 3.

In one embodiment, since the image data corresponding to each angle includes a light spot and a shading, three-dimensional image data reconstructed based on the image data corresponding to each of the respective angles includes a light spot body corresponding to the light spots and a shading body corresponding to the shadings. In this way, since the center point of the light spot body can represent the treatment isocenter and the center point of the shading body can represent the radiotherapy equipment isocenter, the processing device 4 can determine the offset between the radiotherapy equipment isocenter and the treatment isocenter based on the center point of the light spot body and the center point of the shading body.

The following describes examples of the process of determining the offset between the radiotherapy equipment isocenter and the treatment isocenter by back-projecting both the light spot and the shading:

Example 1, the gantry 11 rotates a small number of times. For example, when the gantry 11 rotates once, the processing device 4 can acquire projection data at the two angles with one angle being before the rotation and the other angle being after the rotation. Then the processing device 4 back-projects the light spots and the shadings in the image data at the two angles to the radiotherapy equipment isocenter. In other words, the processing device uses the radiotherapy equipment isocenter to establish a three-dimensional coordinate system. In this three-dimensional coordinate system, according to the image data (which is planar image data) at the two angles, a three-dimensional light spot body and shading body is constructed by using a three-dimensional reconstruction algorithm (because a small number of angles are used, the reconstructed light spot body and shading body may be irregular, that is to say, in the case of a small number of angles, the shape of the reconstructed shading body may be quite different from the shape of the radiation blocking body 3). Then, the offset between the radiotherapy equipment isocenter and the treatment isocenter is determined based on the light spot body and the shading body.

When the gantry 11 rotates a small number of times, the calculation process can be reduced, thereby reducing the processing burden of the processing device 4. This case is suitable for a small offset between the radiotherapy equipment isocenter and the treatment isocenter, which can improve the checking speed.

Example 2, since there may be a gap between each radiation source and a corresponding radiation source mounting hole in the treatment head 12, tiny movements of the radiation source in the radiation source mounting hole may affect the result. To solve this problem, the number of rotations of the gantry 11 may be increased. This example is specifically as follows.

A total angle of rotation of the gantry 11 of the radiotherapy equipment relative to the initial position is 360 degrees, and the gantry is rotated by a preset angle each time.

In the case that the total angle of rotation remains the same, for example, the total angle of rotation is 360 degrees, the smaller the value of the preset angle is, the larger the number of rotations is, the more regular the constructed three-dimensional image is, the closer the shape of the shading body is to the radiation blocking body 3, and the more accurate the result is. Those skilled in the art may set the value of the preset angle according to actual situations. For example, the preset angle may be 0.5 degree, or the preset angle may be 1 degree, and so on. This embodiment takes 0.5 degree as an example, i.e., the gantry 11 of the radiotherapy equipment is rotated by an angle of 0.5 degree each time.

In one embodiment, the position of the gantry 11 before rotation can be called the initial position. The initial position of the gantry 11 is set arbitrarily by those skilled in the art, and the angle of the gantry 11 at the initial position is recorded as 0 degrees. Starting from the initial position, for each rotation, the gantry 11 is rotated by the preset angle, the detector 2 acquires projection data once and sends the projection data at the current angle to the processing device 4, and the processing device 4 generates image data at said angle.

As mentioned above, the processing device 4 determines one batch of image data corresponding to each position of the gantry 11. If the gantry 11 is rotated by an angle of 0.5 degree each time, then: when the gantry 11 is at the initial position, the detector 2 sends projection data corresponding to 0 degrees to the processing device 4, and the processing device 4 generates image data corresponding to 0 degrees; when the gantry 11 is rotated by 0.5 degree relative to the initial position, the detector 2 sends projection data corresponding to 0.5 degree to the processing device 4, and the processing device 4 generates image data corresponding to 0.5 degree; when the gantry 11 is rotated by 1 degree relative to the initial position, the detector 2 sends projection data corresponding to 1 degree to the processing device 4, and the processing device 4 generates image data corresponding to 1 degree; and so on. As shown in Table 1, after the gantry 11 is rotated by 360 degrees relative to the initial position, the processing device 4 acquires 720 batches of image data corresponding to the angles (the image data generated when the gantry 11 is at 0 degrees is the same as that at 360 degrees, and either of the two may be selected, so a total of 720 batches of image data are acquired).

TABLE 1

Image data at different rotation angles relative to the initial position

| Angle relative to initial position | Image data |
| --- | --- |
| 0 | Image data 1 |
| 0.5 | Image data 2 |
| 1 | Image data 3 |
| 1.5 | Image data 4 |
| . . . | . . . |
| 359 | Image data 719 |
| 359.5 | Image data 720 |

In this way, the processing device 4 back-projects the light spots and the shadings in the image data at all the angles to the radiotherapy equipment isocenter, and constructs a light spot body and a shading body according to a three-dimensional reconstruction algorithm. If the light spot is circular and the radiation blocking body 3 is spherical, the constructed light spot body and shading body are both close to a sphere. Subsequently, the processing device 4 can determine the offset between the radiotherapy equipment isocenter and the treatment isocenter based on the light spot body and the shading body, for example, based on the center points of the two or based on edges of the two.

In this way, the processing device 4 uses the image data at a plurality of angles. For example, if 720 batches of image data are used and the treatment head 12 includes 13 radiation sources, each batch of image data includes 13 light spots and shadings. Further, the light spot body and the shading body constructed by the processing device 4 are determined by 9360 light spots having a shading therein. As can be seen, even if there is a gap between one of the radiation source and the radiation source mounting hole and the radiation source undergoes tiny movements in the radiation source mounting hole, the tiny movements have little impact on the final offset between the light spot and the shading. Therefore, by using the above method, the processing device 4 can improve the accuracy of determining the offset between the treatment isocenter and the radiotherapy equipment isocenter.

In the embodiments of the present disclosure, when consistency between a radiotherapy equipment isocenter and a treatment isocenter is checked by the above method, the processing device, after acquiring projection data including a light spot representative of the treatment isocenter and a shading representative of the radiotherapy equipment isocenter, directly converts the projection data into image data without the participation of operator; then the processing device determines an offset between the treatment isocenter and the radiotherapy equipment isocenter based on the image data. As can be seen, in comparison with the checking of consistency between a radiotherapy equipment isocenter and a treatment isocenter by using a film in the related art, the radiation blocking body is not affected by the radiation beam and does not need to be frequently replaced, and the processing device directly converts the projection data into image data without the participation of operator. Therefore, the method simplifies the checking process, and further improves the checking efficiency.

The present disclosure further provides a system for checking consistency between a radiotherapy equipment isocenter and a treatment isocenter. As shown in FIG. 1, the system includes radiotherapy equipment 1, a radiation blocking body 3 and a processing device 4, wherein:

the radiotherapy equipment 1 includes a gantry 11, the gantry 11 is equipped with a treatment head 12 and a detector 2, the detector 2 is mounted on a position opposite to the treatment head 12, and the detector 2 is configured to receive a radiation beam generated by the treatment head 12 and convert the radiation beam into projection data. The radiation blocking body 3 is detachably mounted at the radiotherapy equipment isocenter, and the center of the radiation blocking body 3 coincides with the radiotherapy equipment isocenter. The processing device 4 is electrically connected to the detector 2.

The processing device 4 is mainly configured to execute the method for checking consistency between a radiotherapy equipment isocenter and a treatment isocenter according to the above embodiments, for example: acquiring projection data from the detector 2, and generates image data based on the projection data; wherein the image data includes a light spot and a shading located in the light spot, and the light spot and the shading are formed by a radiation beam generated by the treatment head 12 and being blocked by the radiation blocking body 3; and determining the offset between the radiotherapy equipment isocenter and the treatment isocenter based on an offset between the light spot and the shading in the image data.

The process of determining the offset between the light spot and the shading, the process of determining the offset between the radiotherapy equipment isocenter and the treatment isocenter for a multi-source radiotherapy equipment, and the process of determining the offset between the radiotherapy equipment isocenter and may be a rotary the treatment isocenter in the three-dimensional space by the processing device 4 have been introduced in detail above, reference can be made to the above content, and the details are not repeated here. The following mainly describes the structure of the system.

In one embodiment, the shape and size of the gantry 11 are set according to actual situations, and the treatment head 12 is mounted at the preset position on the gantry 11, as shown in FIG. 1. As mentioned above, the gantry 11 may be a rotatable gantry. Correspondingly, for a single-source radiotherapy equipment, the radiotherapy equipment isocenter is set by those skilled in the art based on an intersection between the axis of rotation of the gantry 11 and the central axis of the radiation beam. For a multi-source radiotherapy equipment, the radiotherapy equipment isocenter is set by those skilled in the art based on the converging point of a plurality of radiation beams on the axis of rotation, that is to say, the converging point is an intersection of the central axes of most of the radiation beams, and also falls on the axis of rotation of the gantry 11. The horizontal dashed line in FIG. 1 represents the axis of rotation of the gantry 11, and point O represents the position of the radiotherapy equipment isocenter.

Figure 5:
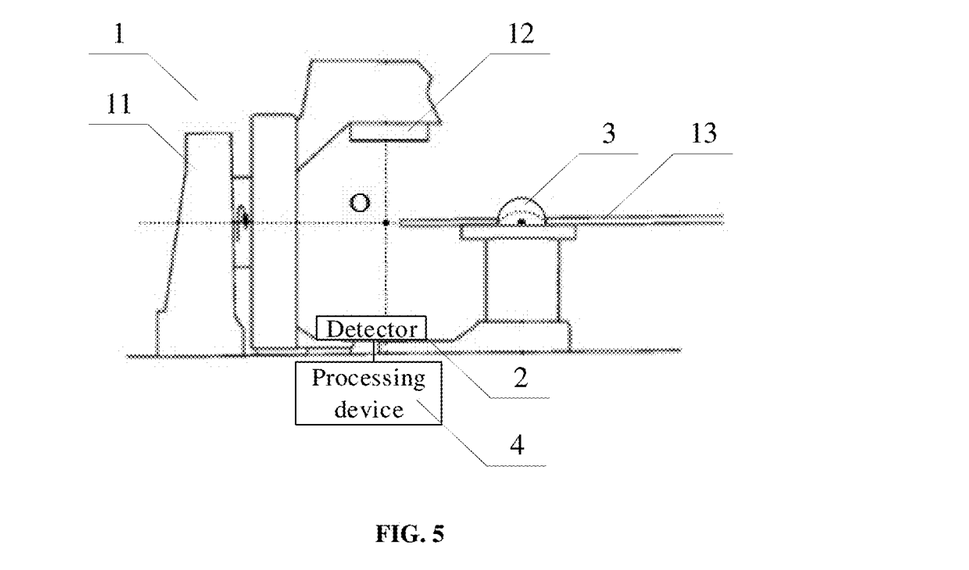
FIG. 5 is a schematic structural diagram of a system for checking consistency between a radiotherapy equipment isocenter and a treatment isocenter according to another embodiment of the present disclosure.

In practice, as shown in FIG. 5, the radiotherapy equipment 1 further includes a treatment couch 13. The radiation blocking body 3 may be mounted at a preset position on the treatment couch 13. During radiotherapy using the radiotherapy equipment 1, a patient lies on the treatment couch 13; next, operator can first adjust the height of the treatment couch 13 so that the patient's ward is at the same height as the radiotherapy equipment isocenter of the radiotherapy equipment 1; then operator moves the treatment couch 13 toward the inside of the gantry 11, so that the patient's ward is located at the radiotherapy equipment isocenter of the radiotherapy equipment 1. It can be seen that the degree of coincidence between the radiotherapy equipment isocenter of the radiotherapy equipment 1 and the treatment isocenter directly affects the quality of radiotherapy. Therefore, operator needs to verify the precision of the radiotherapy equipment 1 periodically or before using the radiotherapy equipment 1.

Optionally, the radiation blocking body 3 is a radiation blocking ball, which is in any spherical structure that can block the penetration of radiation beams, and may be a metal ball, for example, a tungsten ball.

Figure 6:
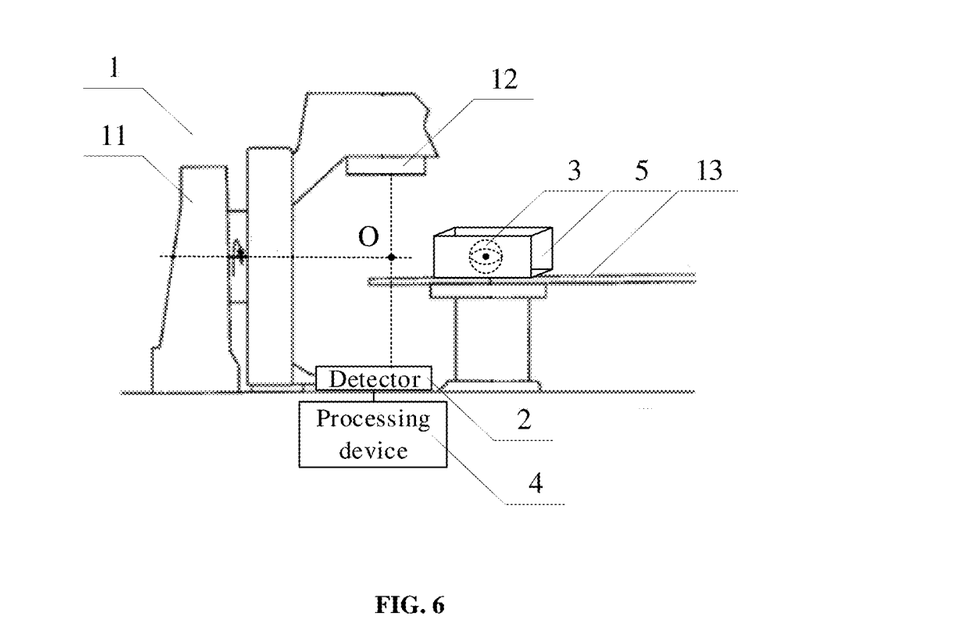
FIG. 6 is a schematic structural diagram of a system for checking consistency between a radiotherapy equipment isocenter and a treatment isocenter according to still another embodiment of the present disclosure.

Optionally, in order to facilitate the mounting of the radiation blocking body 3 on the radiotherapy equipment 1, as shown in FIG. 6, the system further includes a checking phantom 5, the radiation blocking body 3 is mounted at a central position of the checking phantom 5, and the radiation blocking body 3 is detachably mounted at the radiotherapy equipment isocenter by means of the checking phantom 5.

In one embodiment, the checking phantom 5 is detachably mounted at a preset position on the treatment couch 13, and is located at the radiotherapy equipment isocenter. The checking phantom 5 is a box of any shape, for example, as shown in FIG. 6, the checking phantom 5 is a cubic box. After operator secures the checking phantom 5 to the preset position on the treatment couch 13, the operator can adjust the height of the treatment couch 13, so that the radiotherapy equipment isocenter of the radiotherapy equipment 1 is at the same height as the center of sphere of the radiation blocking body 3. Subsequently, the operator moves the treatment couch 13 toward below the treatment head 12, so that the center of the radiation blocking body 3 coincides with the radiotherapy equipment isocenter of the radiotherapy equipment 1. For example, if the radiation blocking body is a radiation blocking ball, the center of sphere of the radiation blocking body 3 coincides with the radiotherapy equipment isocenter of the radiotherapy equipment 1. Finally, the operator turns on the treatment head 12, and the treatment head 12 emits a radiation beam outward.

Figure 7:
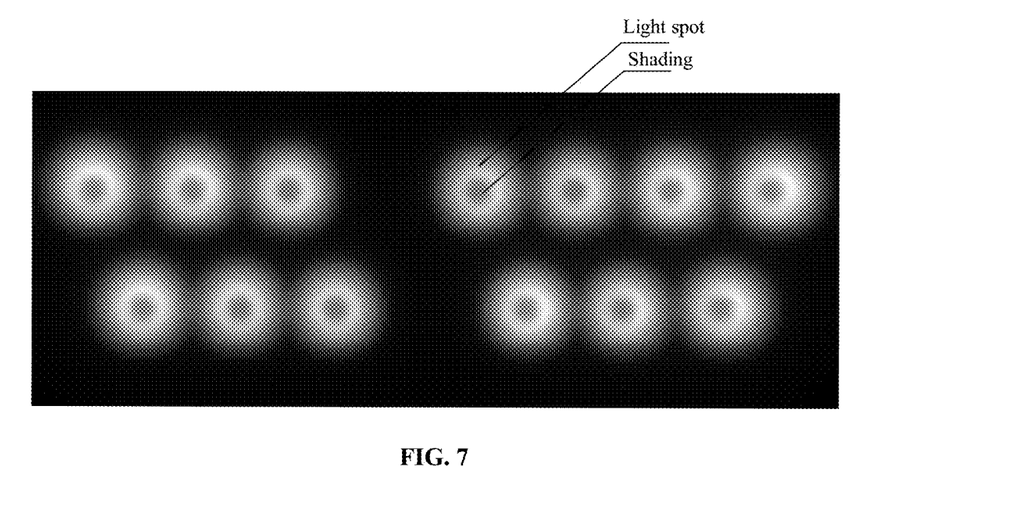
FIG. 7 is a schematic structural diagram of light spots and shadings according to an embodiment of the present disclosure.

Optionally, Below the treatment head 12 is mounted a collimator configured to limit the shape and size of the radiation beam. The shape of the collimator is related to the radiation therapy equipment, i.e., radiotherapy equipment 1. For example, if the radiation therapy equipment, i.e., radiotherapy equipment 1 is a multi-source radiotherapy equipment, the treatment head 12 may include 13 cobalt sources. In this situation, each cobalt source can correspond to one collimator. The collimator adjusts the shape of the cross-section of the radiation beam to a circle. Correspondingly, the shapes of the light spot and the shading in the image data acquired by the processing device 4 are as shown in FIG. 7. For another example, if the radiation therapy equipment, i.e., radiotherapy equipment 1 is a conformal intensity-modulated radiotherapy equipment, the treatment head 12 may include an accelerator. A collimator mounted below the accelerator may be a multi-leaf collimator. The multi-leaf collimator adjusts the shape of the radiation beam to any shape, for example, adjusts the shape of the radiation beam to a square. In this situation, the shapes of the light spot and the shading in the image data acquired by the processing device 4 are as shown in FIG. 8. For example, if the radiotherapy equipment 1 is X-ray radiotherapy equipment, the treatment head 12 includes an accelerator. A collimator mounted below the accelerator is cylindrical, and is also be called a light limiting cylinder. Correspondingly, the shapes of the light spot and the shading in the image data acquired by the processing device 4 may be as shown in FIG. 3.

In the embodiments of the present disclosure, when consistency between a radiotherapy equipment isocenter and a treatment isocenter is checked by using the above system, the processing device, after acquiring projection data including a light spot representative of the treatment isocenter and a shading representative of the radiotherapy equipment isocenter, directly converts the projection data into image data without the participation of operator; then the processing device determines an offset between the treatment isocenter and the radiotherapy equipment isocenter based on the image data. As can be seen, in comparison with the checking method by using a film in the related art, the radiation blocking body is not affected by the radiation beam and does not need to be frequently replaced, and the processing device directly converts the projection data into image data without the participation of operator. Therefore, the system simplifies the checking process, and further improves the checking efficiency.

The present disclosure further provides a device for checking consistency between a radiotherapy equipment isocenter and a treatment isocenter, wherein the device includes a processor and a memory, the memory stores at least one instruction thereon, and the instruction is loaded and executed by the processor to implement the following method for checking consistency between a radiotherapy equipment isocenter and a treatment isocenter:

acquiring projection data from a detector, and generating image data based on the projection data; wherein the image data includes a light spot and a shading located in the light spot, and the light spot and the shading are formed by a radiation beam generated by a treatment head of the radiotherapy equipment and then being blocked by a radiation blocking body;

determining an offset between the radiotherapy equipment isocenter and the treatment isocenter based on the image data.

Optionally, determining the offset between the radiotherapy equipment isocenter and the treatment isocenter based on the image data includes:

determining the offset between the radiotherapy equipment isocenter and the treatment isocenter based on an offset between the light spot and the shading in the image data.

Optionally, acquiring projection data from the detector, and generating the image data based on the projection data includes:

acquiring projection data corresponding to a first preset angle from the detector and generating first image data when a gantry of the radiotherapy equipment is rotated by the first preset angle; and acquiring projection data corresponding to a second preset angle from the detector and generating second image data when the gantry of the radiotherapy equipment is rotated by the second preset angle; and determining the offset between the radiotherapy equipment isocenter and the treatment isocenter based on the offset between the light spot and the shading in the image data includes:

determining a three-dimensional offset between the light spot and the shading based on a two-dimensional offset between the light spot and the shading in the first image data and based on a two-dimensional offset between the light spot and the shading in the second image data; and determining the offset between the radiotherapy equipment isocenter and the treatment isocenter based on the three-dimensional offset between the light spot and the shading.

Optionally, the image data includes a plurality of light spots and shadings located in each light spot; and determining the offset between the radiotherapy equipment isocenter and the treatment isocenter based on the three-dimensional offset between the light spot and the shading includes:

determining an average offset based on a three-dimensional offset between each light spot and the shading included therein in the image data; and determining the offset between the radiotherapy equipment isocenter and the treatment isocenter based on the average offset.

Optionally, the first preset angle differs from the second preset angle by 90 degrees.

Optionally, determining the offset between the radiotherapy equipment isocenter and the treatment isocenter based on the image data includes:

determining the offset between the radiotherapy equipment isocenter and the treatment isocenter based on an offset between a center point of the light spot and a center point of the shading in the image data.

Optionally, acquiring the projection data from the detector, and generating the image data based on the projection data includes:

acquiring, each time the gantry of the radiotherapy equipment is rotated by a different angle relative to an initial position, projection data corresponding to each of the respective angles from the detector and generating image data corresponding to each of the respective angles; and determining the offset between the radiotherapy equipment isocenter and the treatment isocenter based on the image data includes:

determining the offset between the radiotherapy equipment isocenter and the treatment isocenter based on the image data corresponding to each of the respective angles.

Optionally, determining the offset between the radiotherapy equipment isocenter and the treatment isocenter based on the image data corresponding to each of the respective angles includes:
  determining the offset between the radiotherapy equipment isocenter and the treatment isocenter by back-projecting the image data corresponding to each of the respective angles to the radiotherapy equipment isocenter.

Optionally, determining the offset between the radiotherapy equipment isocenter and the treatment isocenter by back-projecting the image data corresponding to each of the respective angles to the radiotherapy equipment isocenter includes:
  back-projecting the light spot in the image data corresponding to each of the respective angles to the radiotherapy equipment isocenter, and constructing a light spot body according to a three-dimensional reconstruction algorithm; and
  determining the offset between the radiotherapy equipment isocenter and the treatment isocenter according to an offset between a center of the light spot body and the radiotherapy equipment isocenter.

Optionally, determining the offset between the radiotherapy equipment isocenter and the treatment isocenter by back-projecting the image data corresponding to each of the respective angles to the radiotherapy equipment isocenter includes:
  back-projecting the light spot and the shading in the image data corresponding to each of the respective angles to the radiotherapy equipment isocenter, and constructing a light spot body and a shading body according to a three-dimensional reconstruction algorithm; and
  determining the offset between the radiotherapy equipment isocenter and the treatment isocenter based on an offset between a center of the light spot body and a center of the shading body.

Optionally, the gantry of the radiotherapy equipment is rotated by an angle of 0.5 degree each time.

Optionally, the shading formed by the radiation blocking body is a centrosymmetric pattern.

Optionally, the shading is in a circular shape, the light spot is in a circular shape, and a diameter of the light spot is greater than or equal to twice of the diameter of the shading.

In the embodiments of the present disclosure, when consistency between a radiotherapy equipment isocenter and a treatment isocenter is checked by the above device, the processor, after acquiring projection data including a light spot representative of the treatment isocenter and a shading representative of the radiotherapy equipment isocenter, directly converts the projection data into image data without the participation of operator; then the processing device determines an offset between the treatment isocenter and the radiotherapy equipment isocenter based on the image data. As can be seen, in comparison with the checking of consistency between a radiotherapy equipment isocenter and a treatment isocenter by using a film in the related art, the radiation blocking body is not affected by the radiation beam and does not need to be frequently replaced, and the processing device directly converts the projection data into image data without the participation of operator. Therefore, the device simplifies the checking process, and further improves the checking efficiency.

It should be noted that: when the apparatus for checking consistency between a radiotherapy equipment isocenter and a treatment isocenter provided by the above embodiments checks the consistency between the radiotherapy equipment isocenter and the treatment isocenter, the description is given by taking the above division of functional modules as an example. In practice, the above functions may be assigned to be implemented by different functional modules according to needs, i.e., the internal structure of the apparatus may be divided into different functional modules to implement all or part of the functions described above. In addition, the apparatus for checking consistency between a radiotherapy equipment isocenter and a treatment isocenter provided by the above embodiments belongs to the same concept as the embodiment of the method for checking consistency between a radiotherapy equipment isocenter and a treatment isocenter. For its specific implementation process, see the method embodiment for details, which will not be repeated here.

The present disclosure further provides a computer readable storage medium, wherein the storage medium stores at least one instruction therein, and the instruction is loaded and executed by a processor to implement the method for checking consistency between a radiotherapy equipment isocenter and a treatment isocenter according to any one of the above implementations.

The structure, features, and effects of the present disclosure are described in detail above based on the embodiments shown in the drawings. The above descriptions are only exemplary embodiments of the present disclosure, and the scope of implementation of the present disclosure is not to be limited by the drawings. Any changes made in accordance with the concept of the present disclosure, or equivalent embodiments with equivalent changes, which do not go beyond the spirit covered by the specification and drawings, shall fall within the scope of protection of the present disclosure.

What is claimed is:

1. A method for checking a consistency between a radiotherapy equipment isocenter and a treatment isocenter, the method comprising:
  acquiring projection data from a detector and generating image data based on the projection data, wherein the image data comprises a light spot and a shading located in the light spot, and the light spot and the shading are formed by a radiation beam generated by a treatment head of the radiotherapy equipment and then being blocked by a radiation blocking body; and
  determining an offset between the radiotherapy equipment isocenter and the treatment isocenter based on the image data.

2. The method according to claim 1, wherein said determining the offset between the radiotherapy equipment isocenter and the treatment isocenter based on the image data comprises:
  determining the offset between the radiotherapy equipment isocenter and the treatment isocenter based on an offset between the light spot and the shading in the image data.

3. The method according to claim 2, wherein said acquiring the projection data from the detector and generating the image data based on the projection data comprises:
  acquiring, in response to a gantry of the radiotherapy equipment being rotated by a first preset angle, projection data corresponding to the first preset angle from the detector and generating first image data; and
  acquiring, in response to the gantry of the radiotherapy equipment being rotated by a second preset angle, projection data corresponding to the second preset angle from the detector and generating second image data, and wherein said determining the offset between the radiotherapy equipment isocenter and the treatment isocenter based on the offset between the light spot and the shading in the image data comprises:

determining a three-dimensional offset between the light spot and the shading based on a two-dimensional offset between the light spot and the shading in the first image data and a two-dimensional offset between the light spot and the shading in the second image data; and determining the offset between the radiotherapy equipment isocenter and the treatment isocenter based on the three-dimensional offset between the light spot and the shading.

4. The method according to claim 3, wherein the image data comprises a plurality of light spots and a plurality of shadings in one-to-one correspondence with the plurality of light spots, and wherein said determining the offset between the radiotherapy equipment isocenter and the treatment isocenter based on the three-dimensional offset between the light spot and the shading comprises:

determining an average offset based on three-dimensional offset between each of the plurality of light spots and a shading corresponding to the light spot in the image data; and determining the offset between the radiotherapy equipment isocenter and the treatment isocenter based on the average offset.

5. The method according to claim 3, wherein the first preset angle differs from the second preset angle by 90 degrees.

6. The method according to claim 1, wherein said determining the offset between the radiotherapy equipment isocenter and the treatment isocenter based on the image data comprises:

determining the offset between the radiotherapy equipment isocenter and the treatment isocenter based on an offset between a center point of the light spot and a center point of the shading in the image data.

7. The method according to claim 1, wherein said acquiring the projection data from the detector and generating the image data based on the projection data comprises:

acquiring, in response to a gantry of the radiotherapy equipment being rotated by a different angle relative to an initial position, projection data corresponding to each of respective angles from the detector and generating image data corresponding to each of the respective angles, and wherein said determining the offset between the radiotherapy equipment isocenter and the treatment isocenter based on the image data comprises:

determining the offset between the radiotherapy equipment isocenter and the treatment isocenter based on the image data corresponding to each of the respective angles.

8. The method according to claim 7, wherein said determining the offset between the radiotherapy equipment isocenter and the treatment isocenter based on the image data corresponding to each of the respective angles comprises:

determining the offset between the radiotherapy equipment isocenter and the treatment isocenter by back-projecting the image data corresponding to each of the respective angles to the radiotherapy equipment isocenter.

9. The method according to claim 8, wherein said determining the offset between the radiotherapy equipment isocenter and the treatment isocenter by back-projecting the image data corresponding to each of the respective angles to the radiotherapy equipment isocenter comprises:

back-projecting the light spot in the image data corresponding to each of the respective angles to the radiotherapy equipment isocenter, and constructing a light spot body according to a three-dimensional reconstruction algorithm; and determining the offset between the radiotherapy equipment isocenter and the treatment isocenter based on an offset between a center of the light spot body and the radiotherapy equipment isocenter.

10. The method according to claim 8, wherein said determining the offset between the radiotherapy equipment isocenter and the treatment isocenter by back-projecting the image data corresponding to each of the respective angles to the radiotherapy equipment isocenter comprises:

back-projecting the light spot and the shading in the image data corresponding to each of the respective angles to the radiotherapy equipment isocenter, and constructing a light spot body and a shading body according to a three-dimensional reconstruction algorithm; and determining the offset between the radiotherapy equipment isocenter and the treatment isocenter based on an offset between a center of the light spot body and a center of the shading body.

11. The method according to claim 7, wherein the gantry of the radiotherapy equipment is rotated by an angle of 0.5 degree each time.

12. The method according to claim 1, wherein the shading formed by the radiation blocking body is a centrosymmetric pattern.

13. The method according to claim 1, wherein the shading is in a circular shape, the light spot is in a circular shape, and a diameter of the light spot is greater than or equal to twice of a diameter of the shading.

14. A non-transitory computer readable storage medium storing at least one instruction therein, wherein the at least one instruction is loaded and executed by a processor to implement the method for checking the consistency between the radiotherapy equipment isocenter and the treatment isocenter according to claim 1.

15. A device for checking a consistency between a radiotherapy equipment isocenter and a treatment isocenter, the device comprising:

a processor and a memory storing at least one instruction thereon, wherein the at least one instruction is loaded and executed by the processor to implement a method for checking the consistency between the radiotherapy equipment isocenter and the treatment isocenter, wherein the method comprises:

acquiring projection data from a detector and generating image data based on the projection data, wherein the image data comprises a light spot and a shading located in the light spot, and the light spot and the shading are formed by a radiation beam generated by a treatment head of the radiotherapy equipment and then being blocked by a radiation blocking body; and determining an offset between the radiotherapy equipment isocenter and the treatment isocenter based on the image data.

16. A system for checking a consistency between a radiotherapy equipment isocenter and a treatment isocenter, the system comprising:

radiotherapy equipment, a radiation blocking body, and a processing device, wherein:

the radiotherapy equipment comprises a gantry, the gantry comprises a treatment head and a detector mounted on a position opposite to the treatment head, and the detector is configured to receive a radiation beam generated by the treatment head and convert the radiation beam into projection data;

the radiation blocking body is detachably mounted at the radiotherapy equipment isocenter, and a center of the radiation blocking body coincides with the radiotherapy equipment isocenter; and the processing device is electrically connected to the detector, and the processing device is configured to execute a method for checking the consistency between the radiotherapy equipment isocenter and the treatment isocenter, wherein the method comprises:

acquiring projection data from the detector and generating image data based on the projection data, wherein the image data comprises a light spot and a shading located in the light spot, and the light spot and the shading are formed by a radiation beam generated by the treatment head of the radiotherapy equipment and then being blocked by the radiation blocking body; and determining an offset between the radiotherapy equipment isocenter and the treatment isocenter based on the image data.

17. The system according to claim 16, wherein the radiation blocking body is a radiation blocking ball.

18. The system according to claim 17, wherein the radiation blocking ball is a metal ball.

19. The system according to claim 16, further comprising a checking phantom, the radiation blocking body being mounted at a central position of the checking phantom, and the radiation blocking body is detachably mounted at the radiotherapy equipment isocenter by means of the checking phantom.

20. The system according to claim 19, wherein the radiotherapy equipment further comprises a treatment couch, and the checking phantom is detachably mounted at a preset position on the treatment couch and is located at the radiotherapy equipment isocenter.

* * * * *